United States Patent [19]

Hoffmeister et al.

[11] 4,070,494

[45] Jan. 24, 1978

[54] ENTERAL PHARMACEUTICAL COMPOSITIONS

[75] Inventors: Friedrich Hoffmeister; Rudolf Hiltmann; Hartmund Wollweber, all of Wuppertal; Helmut Kramer, Leverkusen, all of Germany

[73] Assignee: Bayer Aktiengesellschaft, Germany

[21] Appl. No.: 640,581

[22] Filed: Dec. 15, 1975

[30] Foreign Application Priority Data

July 9, 1975 Germany ............................. 2530563

[51] Int. Cl.$^2$ ...................... A01N 17/00; G01N 1/00; G01N 33/16
[52] U.S. Cl. .......................................... 424/2; 424/10
[58] Field of Search ..................................... 424/2, 10

[56] References Cited

U.S. PATENT DOCUMENTS

| 3,594,477 | 7/1971 | Wollweber et al. ................. 424/263 |
| 3,885,027 | 5/1975 | Shaw et al. ........................... 424/330 |
| 3,980,766 | 9/1976 | Shaw et al. ........................... 424/10 |

Primary Examiner—Stanley J. Friedman
Attorney, Agent, or Firm—Jacobs & Jacobs

[57] ABSTRACT

Enteral pharmaceutical compositions containing medicinal agents having parenteral abuse potential are rendered resistant to aqueous extraction through the incorporation of a sufficient amount of a nontoxic, water gelable material. Attempts to extract the medicinal agent for parenteral abuse are thus inhibited or prevented since the material gels in the presence of water leaving no filterable liquid.

4 Claims, No Drawings

ENTERAL PHARMACEUTICAL COMPOSITIONS

DETAILED DESCRIPTION

It is known that many drugs having a useful and legitimate medical purpose nevertheless have the potential for abuse and extensive legislation has been enacted to control or prevent such abuse; see e.g. 21 U.S.C. 801 et seq. Despite such remedial legislation, the potential for abuse persists as a result of the legitimate presence of these medicinal agents in professional and commercial channels. One form of such abuse involves the extraction of the medicinal agent from an enteral pharmaceutical composition and utilization of the same as a solution for unauthorized, unsupervised and illegal parenteral injection.

The present invention pertains to improvements in such enteral pharmaceutical compositions which inhibit or prevent the abuse of the agent through parenteral injection. The improvement can be utilized with any medicinal agent which can be given orally but which has the potential for parenteral abuse, including those which are now or hereafter included within the various schedules of 21 U.S.C. 812. Since analgesics constitute the largest and most important subgroup of such medicinal agents, the present specification is directed at pharmaceutical compositions containing such analgesics in a form suitable for enteral administration.

It is known that many analgesics of medium to high activity can cause physical and psychic dependence in laboratory animals and, above all, in man. These include many known compounds, some of which are available commercially, such as codeine, pethidine, profadol, anileridines, tilidine, ketobemidone, methadone, alphaprodine, phenapromid, diampromid, propiram and the like. While many of these compounds have recognized value in medicine, they can also be abused by people who are dependent on opiate-like substances. The potential for abuse can differ not only with the particular compound but also on the mode of administration. Generally, dependence liability is considerably greater when the compounds are supplied parenterally than in the case of enteral administration. Consequently it is from the point of view of public health advantageous to prevent parenteral use of pharmaceutical compositions as long as their is no medical reason for such administration. In the form of their salts, however, these analgesics are usually water-soluble and are well tolerated parenterally and accordingly they can be easily extracted from enteral pharmaceutical preparations such as, for example, tablets, dragees, capsules or suppositories, with water. This requires neither a high degree of chemical or pharmaceutical expertise nor specialized apparatus. Since the solutions thus obtained can be administered parenterally, such enteral pharmaceutical forms of these substances have a high potential for abuse. It has been found that the potential for abuse of such medical agents in the form of medicaments which can be used enterally, such as tablets (including lozenges and granules), dragees, capsules, suppositories, pills can be substantially reduced or eliminated by suppressing or inhibiting their extractability from the compositions. As a result, it is not possible to obtain aqueous solutions of sufficient concentration to be suitable for parenteral use.

According to one aspect of the invention therefore, there is provided a method of inhibiting the water extractability from an enteral pharmaceutical composition of a medicinal agent having a high abuse potential which comprises incorporating in said composition, a nontoxic, aqueously gelable material, said gelable material being present in said composition in a quantity at least sufficient to form a gel with substantially no residual filterable liquid when combined with that volume of water otherwise necessary to dissolve all of said medicinal agent.

According to a further embodiment, the present invention pertains to improvements in enteral pharmaceutical compositions containing a medicinal agent having a high abuse potential which improvement comprises incorporating in the composition a nontoxic, aqueously gelable material in a quantity at least sufficient to form a gel with substantially no residual filterable liquid when combined with that quantity of water otherwise necessary to dissolve all of said medicinal agent.

Examples of suitable aqueously gelable materials include methylcelluloses, sodium carboxymethylcellulose, methylhydroxyethylcellulose, methylhydroxypropylcellulose, alginic acid and derivatives or salts thereof, polyacrylic acid, karaya gum and tragacanth or the like. Mixtures of two or more gel-producing substances can be used if desired.

The medicinal agent can include besides a nucleus containing the substances liable to parenteral abuse together with methylcellulose one or more additional active compounds which do not have a high abuse potential, such as acetylsalicylic acid, phenacetin, paracetamol, salicalamide, caffeine, phenylethyl barbituric acid and the like.

The amount of gel-producing substances added will depend both on the nature of the active compound and on the formulation of the composition. In general, it is to be so apportioned that substantially no residual filtrable liquid remains when the medicament is triturated with the minimum amount of water needed to extract the medicinal agent. This is of course somewhat relative since so long as most of the water is utilized in the gelling process, the amount of filtrate will be too small. Addition of large amounts of water results in the concentration of the active compound in the filtrate being too low for effective parenteral administration to the dependent person. In general, the concentration of the aqueously gelable material is from about 5 to about 40% by weight, preferably from about 10 to about 30% by weight, and most desirably between 15 and 20% by weight, of the medicament. Where the medicinal agent is used in combination with one or more other active compounds, the amount and properties of these or each of the other active compounds can have a substantial influence on the amount of gelable material required. For example, suppositories which are each 2 g in weight will in general contain from 30 to 300 mg, preferably typically 50 to 100 mg, of gelable material in each dosage unit. In all formulations, the amount of gelable material in each dosage unit should be at least equal to that of the medicinal agent. The amount of gelable material added can of course be increased as desired above this amount and is limited only by the size of the dosage unit.

Because of the low potential for parenteral abuse, this type of enteral preparations, from which the active substance can no longer be recovered as an aqueous injectable solution, qualify for exemptions from regulations in various countries relating to the prescription of opiate-like substances; e.g. under the Single Convention 1961 (United Nations, 1961, page 45).

Using propiram, which is known to have both morphine-like analgesic action and morphine-antagonistic properties, the following demonstrates how the addition of one of the abovementioned synthetic or natural gelable materials, such as a methylcellulose, to a tablet or suppository composition inhibits extraction with water. In contrast, up to 45% of the same medicinal agent incorporated in tablets and suppositories which were produced without methylcellulose can be extracted in a simple manner. Six 25 mg propiram fumarate tablets (produced according to Example 1) having a total content of 150 mg of propiram fumarate, six 50 mg propiram fumarate tablets (produced according to Example 2) having a total content of 300 mg of medicinal agent, and three 50 mg propiram suppositories (produced according to Example 15) having a total content of 150 mg of active ingredient, were used. Conventional tablets and suppositories produced according to Examples 1, 2 and 15, respectively, but without methylcellulose were used for comparison. The lacquer coatings were peeled off the tablets and the tablet cores were coarsely crushed and extracted for 15 minutes with water at room temperature. The suppositories were coarsely crushed with the aid of a fork and extracted for 15 minutes with water at room temperature.

Samples were filtered either through moistened surgical cotton or through a fluted filter (J. C. Binzer Everol B/MDS φ 20/8153). The propiram in the filtrates was determined by UV spectrophotometric measurement at 258 nm. Since in all tests filtration through the paper filters gave lower yields than when surgical cotton was used, filtration through cotton was used for the control preparations. The results are summarized in Table 1:

in no way reduces the biological availability of the active compound. This can be shown pharmacologically in the tail flick test. The tails of male rats weighing 130 to 150 g are irradiated with a focused heat ray. Untreated animals react after an irradiation time of on average 5.1 ± 0.9 seconds (reaction time) by drawing away their tails. Under the influence of substances having an analgesic action, this reaction time is prolonged. Animals for which the reaction time after administration of a substance is at least 20 seconds are regarded an analgetic. 5 animals are employed per dose and the test period is 90 to 180 minutes. The $ED_{50}$ is the dose at which the reaction time is prolonged to at least 20 seconds in, on average, 50% of the animals employed. (See generally Wolff et al., J. Clin. Invest., 19, 659–680 (1940).

The results are shown in Table 2.

Table 2

Effect of propiarm tablets with and without added 4,000 cp methyl cellulose in the heat radiation test on rats' tails

| Substance | Tail flick test rat De 50 mg/kg p.o.* | Relative potency** | Significantly different |
|---|---|---|---|
| propiram tablets according to formulation of Example 1 | 18.3(13.2–22.5) | 1.16(0.88–1.57) | no |
| propiram tablets without 4,000 cp methylcellulos | 21.2(16.6–26.7) | 1.00 | — |

*Statistical calculation: probit analysis according to Fink and Hund (1965)
**Statistical calculation: probit analysis according to Fink, Hund and Meysing (1966)

Whereas propiram is treated as an opiate (Schedule

Table 1

Solubility test on propiram tablets with and without added 4,000 cp methylcellulose

| Number of tablets or suppositories/ amount of Propiram | Amount of distilled water used for the extraction (ml) | Type of filter | Filtrate Milli-liters | Filtrate Yield % | Concentration in the filtrate mg/ml | Concentration in the filtrate % | Yield of Propiram in %, calculated with respect to the amount employed |
|---|---|---|---|---|---|---|---|
| 6×50 mg tablets = 300 mg Formulation Example 2 | 10 | Cotton | φ | φ | φ | φ | φ |
|  | 10 | Filter | φ | φ | φ | φ | φ |
|  | 20 | Cotton | 2.6 | 13 | 5.06/2.6 | 0.19 | 1.69 |
|  | 20 | Filter | φ | φ | φ | φ | φ |
| Control without 4,000 cp methylcellulose | 10 | Cotton | 4.6 | 46.0 | 118.5/4.6 | 2.58 | 39.5 |
|  | 20 | Cotton | 13.8 | 69.0 | 98.1/13.8 | 0.71 | 32.7 |
| 6×25 mg tablets = 150 mg Formulation Example 1 | 10 | Cotton | 1.5 | 15.0 | 1.87/1.5 | 0.12 | 1.25 |
|  | 10 | Filter | φ | φ | φ | φ | φ |
|  | 20 | Cotton | 10 | 50 | 13.3/1.0 | 0.13 | 8.9 |
|  | 20 | Filter | 1.0 | 5.0 | 2.55/1.0 | 0.26 | 1.7 |
| Control without 4,000 cp methylcellulose | 10 | Cotton | 5.6 | 56.0 | 64.9/5.6 | 1.16 | 43.3 |
|  | 20 | Cotton | 14.2 | 71.0 | 52.9/14.2 | 0.39 | 35.3 |
| 3×50 mg suppositories = 150 mg Formulation, Example 15 | 10 | Cotton | φ | φ | φ | φ | φ |
|  | 10 | Filter | φ | φ | φ | φ | φ |
|  | 20 | Cotton | 9 | 45 | 15.2/9.0 | 0.17 | 10.1 |
|  | 20 | Filter | 3.6 | 18 | 4.4/3.6 | 0.12 | 2.9 |
| Control without 4,000 cp methylcellulose | 10 | Cotton | 5.9 | 59.0 | 57.2/5.9 | 0.97 | 38.1 |
|  | 20 | Cotton | 14.0 | 70.0 | 48.0/14.0 | 0.34 | 32.0 |

The results summarized in Table 1 clearly show that the extractability with water of the active compound, which in itself is readily water-soluble, can be severely inhibited or completely prevented by adding a water gelable material, such as a methylcellulose. The potential for abuse of these preparations is thus substantially reduced. One might assume that the biological availability of water-soluble medicinal agent when administered in the intended fashion would also be adversely affected in such compositions. Surprisingly the addition of one or more water gelable materials to enteral preparations II, Single Convention 1961), the WHO and the United Nations Narcotic Commission regard compositions of propiram prepared in accordance with this invention to have an abuse liability reduced to such an extent that such tablet formulations have been exempted from the regulations relating to the prescription of such substances and thus classified in Schedule III (Single Convention 1961).

Formulation Examples 1 to 16

1. Tablets containing 25 mg of propiram

Part A 3.55 kg of propiram fumarate, corresponding to 2.5 kg of propiram
4.85 kg of lactose
3.00 kg of cellulose powder
3.00 kg of methylcellulose
3.00 kg of maize starch and
0.05 kg of highly disperse silica were mixed and the mixture is compressed once by means of a tablet press. The compressed tablets are subsequently sieved through a sieve of 3.0 mm mesh width and then through a sieve of 0.8 mm mesh width. 0.05 kg of magnesium stearate is then admixed with the mixture.

This gives a total weight of 17.50 kg.

Tablets 175.0 mg in weight and 8 mm in diameter are produced from the mixture in a tablet press. The tablets are then coated in a coating kettle by a known process using a lacquer which is not resistant to gastric juices and which is based on hydroxypropylmethylcellulose. The tablets decompose in water at 37° C in a maximum of 15 minutes.

2. Tablets containing 50 mg of Propiram

|  |  |
|---|---|
| 7.10 kg of Propiram fumarate = 5.0 kg of Propiram | |
| 9.70 kg of lactose | |
| 6.00 kg of cellulose powder | |
| 6.00 kg of methylcellulose | |
| 6.00 kg of maize starch | |
| 0.10 kg of highly disperse silica and | |
| 0.10 kg of magnesium stearate | |
| Total: | 35.00 kg |

Tablets are produced according to the procedure indicated in Example 1. The resulting tablets, which are 350 mg in weight and 10.3 mm in diameter, are then lacquered.

3. Combination tablets containing 10 mg of Propiram

Part A 1.42 kg of Propiram fumarate corresponding to 1.0 kg of Propiram
1.94 kg of lactose
1.20 kg of cellulose powder
1.20 kg of methylhydroxyethylcellulose
1.20 kg of maize starch and
0.02 kg of highly disperse silica are mixed and the mixture is compressed once by means of a tablet press. The compressed tablets are subsequently sieved through a sieve of 3.0 mm mesh width and then through a sieve of 0.8 mm mesh width. 0.02 kg of magnesium stearate is then admixed with the mixture. This gives a total of 7.00 kg.

Tablets 70.0 mg in weight and 6 mm in diameter are produced from the mixture in a tablet press. The tablets are then coated in a coating kettle with a lacquer which is not resistant to gastric juices and which is based on hydroxypropylmethylcellulose. The tablets decomposed in water at 37° C in a maximum of 15 minutes.

Part B 25.00 kg of acetylsalicylic acid
3.00 kg of caffeine
12.00 kg of cellulose powder
2.80 kg of maize starch and
0.20 kg of sodium lauryl sulphate are mixed and the mixture is compressed once by means of a tablet press. The compressed tablets are sieved through a sieve of 3.0 mm mesh width and then through a sieve of 0.8 mm mesh width. This gives a total of 43.00 kg.

Tablets which have a total weight of 500 mg, a diameter of 11 mm and a radius of curvature of 15 mm are produced from the tablets prepared under Part A and the mixture prepared under Part B by a known method in a tablet press for the production of coated tablets. The tablet coating decomposes in a maximum of 5 minutes in water at 37° C.

4. Combination tablets containing 25 mg of Propiram

Part A 3.55 kg of Propiram fumarate corresponding to 2.5 kg of Propiram
2.50 kg of methylhydroxypropylcellulose
0.85 kg of lactose
1.00 kg of maize starch
1.00 kg of cellulose powder and
0.10 kg of magnesium stearate are mixed and the mixture is compressed once by means of a tablet press. The compressed tablets are subsequently sieved through a sieve of 3.00 mm mesh width and then through a sieve of 0.8 mm mesh width. This gives a total of 9.00 kg.

Tablets 90 mg in weight and 6 mm in diameter were produced from the mixture in a tablet press. The tablets decompose in water at 37° C in a maximum of 15 minutes.

Part B 25.00 kg of acetylsalicylic acid
1.00 kg of codeine phosphate
14.00 kg of cellulose powder
2.80 kg of maize starch and
0.20 kg of sodium lauryl sulphate are mixed and the mixture is compressed once by means of a tablet press. The compressed tablets are sieved through a sieve of 3.0 mm mesh width and then through a sieve of 0.8 mm mesh width. This gives a total of 43.00 kg.

Tablets which have a total weight of 520.0 mg and a diameter of 11 mm are produced from the tablets prepared under Part A and the mixture prepared under Part B by a known method in a tablet press for the production of coated tablets. The tablet coating decomposes in water at 37° C in a maximum of 5 minutes.

5. Combination tablets containing 25 mg of Propiram

Part A 3.55 kg of Propiram fumarate corresponding to 2.5 kg of Propiram
0.75 kg of cellulose powder
1.10 kg of lactose
2.50 kg of sodium carboxymethylcellulose
1.00 kg of maize starch and
0.10 kg of magnesium stearate are mixed and the mixture is compressed once by means of a tablet press. The compressed tablets are subsequently sieved through a sieve of 3.0 mm mesh width and then through a sieve of 0.8 mm mesh width. This gives a total of 9.00 kg Tablets 90 mg in weight and 6 mm in diameter are produced from the mixture in a tablet press. The tablets decompose in water at 37° C in a maximum of 15 minutes.

Part B 25.00 kg of acetylsalicylic acid
3.00 kg of caffeine
2.50 kg of phenylethylbarbituric acid
1.00 kg of codeine phosphate
8.50 kg of cellulose powder
2.80 kg of maize starch and
0.20 kg of sodium lauryl sulphate
are mixed and the mixture is compressed once by means of a tablet press. The compressed tablets are sieved through a sieve of 3.0 mm mesh width and then through a sieve of 0.8 mm mesh width. This gives a total of 43.00 kg.

Tablets which have a total weight of 520.0 mg and a diameter of 11 mm are produced from the tablets prepared under Part A and the mixture prepared under Part B by a known method in a tablet press for the production of coated tablets. The tablet coating decomposes in water at 37° C in a maximum of 5 minutes.

6. Tablets containing 25 mg of pethidine hydrochloride 2.50 kg of pethidine hydrochloride
5.90 kg of lactose
3.00 kg of cellulose powder
3.00 kg of polyacrylic acid
3.00 kg of maize starch
0.05 kg of highly disperse silica and
0.05 kg of magnesium stearate
This gives a total of 17.50 kg.

The tablets are produced according to the procedure indicated in formulation example 1. The resulting tablets, which each weigh 175 mg, have a diameter of 8 mm and subsequently can be lacquered.

7. Tablets containing 50 mg of Tilidin hydrochloride 5.145 kg of Tilidin hydrochloride semihydrate = 50 kg of Tilidin hydrochloride
11.655 kg of lactose
6.000 kg of cellulose powder
6.000 kg of methylcellulose
6.000 kg of maize starch
0.100 kg of highly disperse silica and
0.100 kg of magnesium stearate
This gives a total of 350.000 kg.

The tablets are produced according to the procedure indicated in formulation example 1. The resulting tablets, which each weigh 350 mg, have a diameter of 10.3 mm and subsequently can be lacquered.

8. Tablets containing 25 mg of Phenampromid hydrochloride 2.50 kg of Phenampromid hydrochloride
5.90 kg of lactose
3.00 kg of cellulose powder
3.00 kg of methylcellulose
3.00 kg of maize starch
0.05 kg of highly disperse silica and
0.05 kg of magnesium stearate
This gives a total of 17.50 kg.

The tablets are produced according to the procedure indicated in formulation example 1. The resulting tablets, which each weigh 175 mg, have a diameter of 8 mm and subsequently can be lacquered.

9. Tablets containing 2.5 mg L-methadone hydrochloride 0.25 kg of L-methadone hydrochloride
8.15 kg of lactose
3.00 kg of cellulose powder
3.00 kg of alginic acid
3.00 kg of maize starch
0.05 kg of highly disperse silica and
0.05 kg of magnesium stearate
This gives a total of 17.50 kg.

The tablets are produced according to the procedure indicated in formulation example 1. The resulting tablets, which each weigh 175 mg, have a diameter of 8 mm and subsequently can be lacquered.

10. Tablets containing 5 mg of ketobemidone hydrochloride 0.50 kg of ketobemidone hydrochloride
7.90 kg of lactose
3.00 kg of cellulose powder
3.00 kg of tragacanth powder
3.00 kg of maize starch
0.05 kg of highly disperse silica and
0.05 kg of magnesium stearate
This gives a total of 17.50 kg.

The tablets are produced according to the procedure indicated in formulation example 1. The resulting tablets, which each weigh 175 mg, have a diameter of 8 mm and subsequently can be lacquered.

11. Tablets containing 15 mg of profadol hydrochloride 1.50 kg of Profadol hydrochloride
6.90 kg of lactose
3.00 kg of cellulose powder
3.00 kg of karaya gum
3.00 kg of maize starch
0.05 kg of highly disperse silica and
0.05 kg of magnesium stearate
This gives a total of 17.50 kg.

The tablets are produced according to the procedure indicated in formulation example 1. The resulting tablets, which each weigh 175 mg, have a diameter of 8 mm and subsequently can be lacquered.

12. Tablets containing 25 mg of anileridine dihydrochloride 2.50 kg of anileridine dihydrochloride
5.90 kg of lactose
3.00 kg of cellulose powder
3.00 kg of methylcellulose
3.00 kg of maize starch
0.05 kg of highly disperse silica and
0.05 kg of magnesium stearate
This gives a total of 17.50 kg.

The tablets are produced according to the procedure indicated in formulation example 1. The resulting tablets, which each weigh 175 mg, have a diameter of 8 mm and subsequently can be lacquered.

13. Tablets containing 10 mg of trimeperidine hydrochloride 1.00 kg of trimeperidine hydrochloride
7.40 kg of lactose
3.00 kg of cellulose powder
3.00 kg of sodium carboxymethylcellulose
3.00 kg of maize starch
0.05 kg of highly disperse silica and 0.05 kg of magnesium stearate This gives a total of 17.50 kg.

The tablets are produced according to the procedure indicated in formulation example 1. The resulting tablets, which each weigh 175 mg, have a diameter of 8 mm and subsequently can be lacquered.

14. Tablets containing 25 mg of prodilidine hydrochloride 2.50 kg of prodilidine hydrochloride
5.90 kg of lactose
3.00 kg of cellulose powder
3.00 kg of methylhydroxyethylcellulose
3.00 kg of maize starch
0.05 kg of highly disperse silica and
0.05 kg of magnesium stearate This gives a total of 17.50 kg.

The tablets are produced according to the procedure indicated in formulation example 1. The resulting tablets, which each weigh 175 mg, have a diameter of 8 mm and subsequently can be lacquered.

15. Suppositories containing 50 mg of propiram

| 0.071 kg | of Propiram fumarate corresponding to 0.050 kg of Propiram |
|---|---|
| 0.100 kg | of methylcellulose and |
| 1.969 kg | of solid fat (cocoa butter) |
| 2.140 kg | = 1,000 suppositories. |

The solid fat is melted in a suitable vessel and the Propiram fumarate and methylcellulose are suspended whilst stirring and suppositories weighing 2 g are produced by a known method by means of a suitable mould.

16. Suppositories containing 25 mg of propiram

| 0.035$^5$ | kg of Propiram fumarate corresponding to 0.025 kg of Propiram |
|---|---|
| 0.075 | kg of tragacanth powder |
| 0.959$^5$ | kg of solid fat |
| 1.070 | kg = 1,000 suppositories. |

The solid fat is melted in a suitable vessel and the Propiram fumarate and tragacanth powder are suspended whilst stirring and suppositories weighing 100 g are produced by a known method by means of a suitable mould.

What is claimed is:

1. In an enterally administered pharmaceutical composition which is a tablet, capsule or suppository containing the medicinal agent having parenteral abuse potential N-(1-methyl-2-piperidinoethyl)-N-pyrid-2-ylpropionamide or an acid addition salt thereof, the improvement inhibiting water extractability of said agent without reducing its biological availability from the composition when administered enterally which comprises the presence in said composition of a nontoxic, aqueously gelable material selected from the group consisting of methylcellulose, sodium carboxymethylcellulose, methylhydroxyethylcellulose, methylhydroxypropylcellulose, alginic acid, polyacrylic acid, karaya gum and tragacanth in a quantity at least equal to the amount of said agent so as to form a gel with substantially no residual filterable liquid when combined with that quantity of water otherwise necessary to dissolve all of said medicinal agent.

2. A pharmaceutical composition according to claim 1 wherein the quantity of the aqueously gelable material is present in an amount from about 5 to about 40% by weight of the composition.

3. A pharmaceutical composition according to claim 2 wherein the quantity of the aqueously gelable material is present in an amount from about 10 to about 30% by weight of the composition.

4. A pharmaceutical composition according to claim 1 wherein the aqueously gelable material is methylcellulose.

* * * * *